United States Patent [19]

Shawl et al.

[11] 4,146,727
[45] Mar. 27, 1979

[54] PROCESS FOR THE PREPARATION OF DIPHENYLMETHANE MONO AND DICARBAMATES AND POLYMETHYLENE POLYPHENYL CARBAMATES BY THE ACID REARRANGEMENT OF AN (ALKOXYCARBONYL) PHENYLAMINOMETHYLPHENYL COMPOUND

[75] Inventors: Edward T. Shawl, Wallingford; John G. Zajacek, Devon, both of Pa.

[73] Assignee: Atlantic Richfield Company, Los Angeles, Calif.

[21] Appl. No.: 905,705

[22] Filed: May 15, 1978

Related U.S. Application Data

[63] Continuation-in-part of Ser. No. 838,691, Oct. 3, 1977, abandoned.

[51] Int. Cl.² .......................................... C07C 125/04
[52] U.S. Cl. ...................................... 560/25; 560/27; 260/453 P
[58] Field of Search ................................. 560/25, 27

[56] References Cited

U.S. PATENT DOCUMENTS

| | | | |
|---|---|---|---|
| 2,946,768 | 7/1960 | Klauke et al. | 260/453 P |
| 3,919,279 | 11/1975 | Rosenthal et al. | 260/453 P |
| 3,956,360 | 5/1976 | Zajacek et al. | 560/25 |

OTHER PUBLICATIONS

Clark, "Chem. Absts.", vol. 57, 13627, 1962.

Primary Examiner—James O. Thomas, Jr.
Assistant Examiner—G. T. Breitenstein
Attorney, Agent, or Firm—Delbert E. McCaslin

[57] ABSTRACT

Diphenylmethane mono and dicarbamates and polymethylene polyphenyl carbamate homologs and derivatives of these compounds are produced by the protonic or Lewis acid catalyzed rearrangement of an (alkoxycarbonyl)phenylaminomethylphenyl compound having the general formula

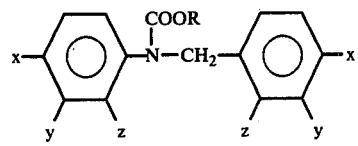

including the higher homologs of such compounds, wherein x, y and z, which are different on the ring, are an alkyl group having from 1 to 3 carbon atoms, an —NHCOOR, —CH$_2$ArNHCOOR or —N(COOR)CH$_2$Ar group; x, y and z may also be at least one hydrogen; R is a 1 to 3 carbon alkyl group and Ar is phenyl which may be substituted with a 1 to 3 carbon atom alkyl group.

19 Claims, No Drawings

PROCESS FOR THE PREPARATION OF DIPHENYLMETHANE MONO AND DICARBAMATES AND POLYMETHYLENE POLYPHENYL CARBAMATES BY THE ACID REARRANGEMENT OF AN (ALKOXYCARBONYL) PHENYLAMINOMETHYLPHENYL COMPOUND

CROSS REFERENCE TO RELATED APPLICATION

This application is a continuation-in-part of application Ser. No. 838,691, filed Oct. 3, 1977, non abandoned.

FIELD OF THE INVENTION

The present invention relates to a process for the preparation of esters of aromatic carbamic acids (urethanes) particularly diphenylmethane dicarbamates and related higher homologs and derivatives, by the acid catalyzed rearrangement of an (alkoxycarbonyl)-phenylaminomethylphenyl compound such as 2-[(ethoxycarboxyl)phenylaminomethyl]phenylcarbamic acid, alkyl esters.

BACKGROUND OF THE INVENTION

Polymeric aromatic carbamic acid esters (polyurethanes) such as diphenylmethane dicarbamates and the related higher homologs polymethylene polyphenyl carbamates have become increasingly important products particularly, for use in the preparation of the commercially valuable diphenylmethane diisocyanates and mixtures of diisocyanates and the polyisocyanates by the decomposition of such polymeric aromatic carbamic acid esters in a suitable solvent as shown in Rosenthal et al., U.S. Pat. Nos. 3,962,302, June 8, 1976 and 3,919,279, Nov. 11, 1975.

At the present time there is no known successful commercial method for the direct preparation of polymeric aromatic esters of carbamic acid. The corresponding diphenylmethane diisocyanates and polyisocyanates, available commercially, are largely produced by the phosgenation of mixtures of diamines and polyamines obtained by the condensation of aniline and formaldehyde with catalytic quantities of a mineral acid, as for example, disclosed in the Pistor et al, U.S. Pat. No. 4,014,914.

A proposed prior art process for the preparation of polymeric aromatic carbamic acid esters (polyurethanes) is disclosed in Klauke et al, U.S. Pat. No. 2,946,768 and involves the condensation of aryl carbamic acid esters with carbonyl compounds in a dilute aqueous acid condensation medium. However, in such process the carbonyl compound such as formaldehyde tends to react at the nitrogen of the carbamate to produce along with desired polyurethanes, varying amounts, i.e., generally between 15 percent and 50 percent by weight, of undesirable (alkoxycarbonyl)-phenylaminomethylphenyl compounds which includes the various dimers, trimers, tetramers, etc. of such compounds (also referred to herein as "N-benzyl" compounds). Attempts to prepare mono or diisocyanates and polyisocyanates or to otherwise use the mixture containing the undesired N-benzyl compounds, which cannot be converted to an isocyanate by pyrolysis, and polyurethanes presents many problems since there is no known method for separating the polyurethanes from the N-benzyl impurities.

SUMMARY OF THE INVENTION

This invention relates to a process for the preparation of diphenylmethane mono and dicarbamates and the higher molecular weight homologs, polymethylene polyphenyl carbamates, which comprises catalytically rearranging an (alkoxycarbonyl)phenylaminomethylphenyl compound (N-benzyl compound) with a particular acid medium. More specifically, the present invention concerns a method for the preparation of the carbamates by the catalyzed rearrangement of the N-benzyl compounds produced, in addition to urethanes, as side products by the condensation of lower alkyl esters of phenyl carbamic acid with carbonyl compounds, such as formaldehyde, in the presence of an aqueous acid solution as described for example in the aforementioned U.S. Pat. No. 2,946,768 and incorporated herein by reference. The product mixture produced by such condensation process containing diurethanes and polyurethanes, N-benzyl compounds, unreacted alkylphenyl-carbamates and other by-products such as amines may be contacted at temperatures of from about 50° C. to 170° C. with a protonic acid medium having a strength at least equal to a 75 percent sulfuric acid such as concentrated sulfuric acid or an acid medium comprising a Lewis acid having a concentration of at least 0.5 percent by weight based on the total reaction mixture, while maintaining a minimum amount of water in the system, to catalytically convert or rearrange said N-benzyl compounds to the desired mono-, di- and polyurethanes. Alternatively, the unreacted alkylphenylcarbamate may be removed from the mixture by, for example, vacuum distillation prior to treatment. The acid rearrangement of the N-benzyl compounds resulting from other methods of preparation, as hereinafter described, is also contemplated by the method of the present invention.

It is an object of this invention therefore to provide a process for the preparation of diphenylmethane mono and dicarbamates and the related polymethylene polyphenyl carbamates in high yield by the conversion or rearrangement of (alkoxycarbonyl)phenylaminomethylphenyl compounds employing a suitable protonic or Lewis acid medium as a catalyst.

It is another object of this invention to provide a process for the acid catalyzed conversion or rearrangement of (alkoxycarbonyl)phenylaminomethylphenyl compounds formed during the preparation of di- and higher polymeric carbamic acid esters by the dilute aqueous acid condensation of N-aryl carbamic acid esters such as ethylphenyl carbamate with a carbonyl compound to the useful di- and polyurethane compounds.

These and other objects and advantages of this invention will become apparent from the description of the invention which follows and from the claims.

DESCRIPTION OF THE INVENTION

In accordance with the present invention, an (alkoxycarbonyl)phenylaminomethylphenyl compound having the general formula

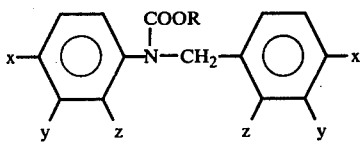

including the higher homologs of compounds, wherein x, y and z, which are different on the ring, are an alkyl group having from 1 to 3 carbon atoms, an —NHCOOR, —CH$_2$ArNHCOOR or —N(COOR)CH$_2$Ar group; x, y and z may also be at least one hydrogen; R is a 1 to 3 carbon alkyl group and Ar is phenyl which may be substituted with a 1 to 3 carbon atom alkyl group, is contacted at temperatures of from about 50° C. to 170° C., preferably under atmospheric pressure, with a catalytic amount of a protonic acid medium having the strength of at least the magnitude of a 75 percent sulfuric acd, or with a Lewis acid medium having a concentration of at least 0.5 percent by weight based on the total reaction mixture, with or without the addition of an inert solvent, to catalytically convert or rearrange the (alkoxycarbonyl)phenylaminomethylphenyl compound mixture to mono or dicarbamates and polymethylene polyphenyl carbamates and derivatives. The preparation of a diphenylmethane dicarbamate, diethyl ester, for example, is carried out according to the following postulated equation employing a 2-[(ethoxycarbonyl)phenylaminomethyl]phenylcarbamic acid, ethyl ester:

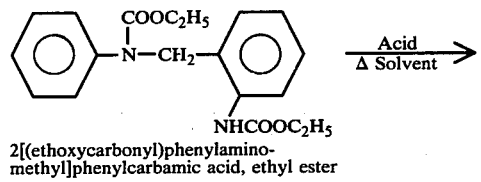

2[(ethoxycarbonyl)phenylaminomethyl]phenylcarbamic acid, ethyl ester

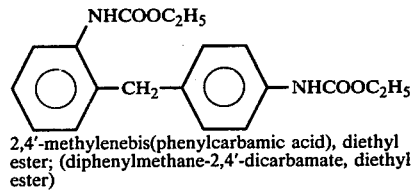

2,4'-methylenebis(phenylcarbamic acid), diethyl ester; (diphenylmethane-2,4'-dicarbamate, diethyl ester)

The acid catalyzed rearrangement reaction may be carried out in any suitable reactor which is generally equipped with a means for agitation. A general procedure is to charge the N-benzyl compounds together with the protonic or Lewis acid catalyst and optionally a solvent into the reaction vessel and then heat the mixture to the desired temperature for the appropriate period. The reaction may be carried out batchwise or as a continuous process and the order of addition of the materials may be varied to suit the particular apparatus employed. The reaction products are recovered and treated by any conventional method such as extraction of the acid medium with water or neutralization with a base and the separation of the resulting phases and distillation to remove any solvent employed, or filtering to remove the catalyst.

The (alkoxycarbonyl)phenylaminomethylphenyl compounds which may be converted or rearranged by the process of the present invention and characterized by the general formula above include, for example, those compounds which may conform to the following formulae wherein R is an alkyl group containing from 1 to 3 carbon atoms:

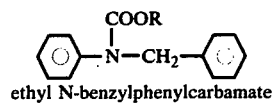

ethyl N-benzylphenylcarbamate

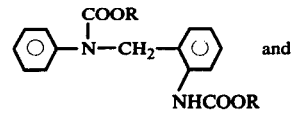

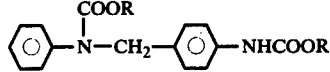

2- and 4-[(alkoxycarbonyl)phenylaminomethyl]phenylcarbamic acid, alkyl ester respectively,

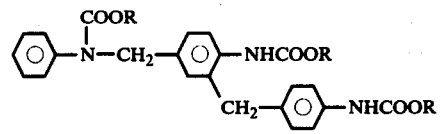

4-[(alkoxycarbonyl)phenylaminomethyl]-2,4'-methylenebis-(phenylcarbamic acid), dialkyl ester,

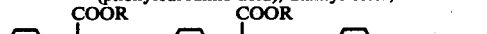

4 and 3[4-[(alkoxycarbonyl)phenylaminoethyl]phenyl(alkoxycarbonyl)aminomethyl]phenylcarbamic acid, alkyl ester respectively; and

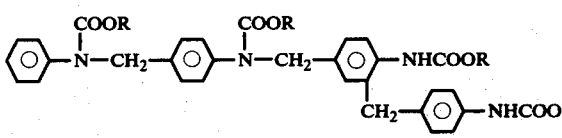

4-[4-[(alkoxycarbonyl(phenylaminomethyl]phenyl(alkoxycarbonyl)aminomethyl]-2,4'-methylenebis(phenylcarbamic acid), dialkyl ester.

These (alkoxycarbonyl)phenylaminomethylphenyl compounds specifically shown by formula and named are obviously merely representative of other N-benzyl compounds, especially the various isomers of such compounds, which fall within the definition of the general formula hereinabove described for the compounds which can be converted or rearranged to the desired carbamates especially the polycarbamates by the method of this invention. In general, the ethyl esters, i.e., where R is a C$_2$H$_5$ group and which are produced during the condensation of ethylphenylcarbamate (phenylurethane) with a carbonyl compound such as formaldehyde, are preferred for the preparation of the diethyl esters of diphenylmethane dicarbamate and polymethylene polyphenyl carbamates which may be decomposed to the valuable polymeric isocyanates as hereinabove described.

As indicated above, the reaction product including the N-benzyl compounds which result in unseparable side products during the condensation of alkyl esters of phenylcarbamic acid such as ethylphenylcarbamate with carbonyl compounds such as formaldehyde in the presence of the dilute aqueous acid solution may be processed according to the method of the present invention as such or after removal of the ethylphenylcarbamate unreacted starting material. In addition, N-benzyl compounds which may be produced by other known methods can be employed in the present process. For example, N-phenylbenzylamine and alkylchloroformate, e.g., methyl, ethyl or propylchloroformate may be reacted to prepare the appropriate alkyl N-benzylphenylcarbamate. N-phenyl-2-aminobenzylamine and N-phenyl-4-aminobenzylamine prepared according to the process shown in British Pat. No. 1,177,557, January, 1970, may be reacted with an excess of the alkylchloroformate, such as ethylchloroformate, to produce 2- and 4-[(ethoxycarbonyl)-phenylaminomethyl]-phenylcarbamic acid, ethyl ester respectively. The 2- and 4-[(alkoxycarbonyl)phenylaminomethyl]phenylcarbamic acid, alkyl esters may also be prepared by reacting a substituted benzyl alcohol such as for example a carbamic acid, benzyl hydroxy, ethyl ester (ethylphenylcarbamate-2-methylol) with ethylphenylcarbamate and an acid catalyst.

The protonic acid medium employed as catalysts and suitable for use in the present invention may be either inorganic or organic provided it is a strong acid and has a strength at least equal to a 75 percent sulfuric acid. The protonic acid catalysts are generally employed in concentrations of from 0.1 to 25 weight percent based on the total reaction mixture and preferably from 1 to 10 weight percent. Higher concentrations may also be employed. Representative protonic acid catalysts especially suitable for use in this invention are concentrated (75 percent or higher) sulfuric acid, p-toluene sulfonic acid, trifluoromethane sulfonic acid, anhydrous hydrofluoric acid, fluorosulfonic acid and strongly acidic sulfonated polyaromatic ion exchange resins (sold, for example, commercially as "Amberlyst 15" by Rohm and Haas Co.) and having a bulk density of approximately 595 g/l., a hydrogen ion concentration of approximately 4.9 milliequivalents/g. dry, a surface area of from about 40 to 50 $m^2$/g. and an average pore diameter of from about 200 to 600 Angstrom units. Mixtures of the acid catalysts may be employed but, it is preferable to use individual acid catalyst in order to lessen any recovery problems.

The Lewis acid catalysts which may be employed as catalysts in the present invention may be, for example, tin (IV)chloride, iron (III)chloride, aluminum chloride, antimony pentafluoride and boron trifluoride. The Lewis acid catalysts which may be supported on, for example, graphite, are employed in concentration of at least 0.5 preferably in a range of from 0.5 to 20 weight percent based on the total reaction mixture. The protonic acids are the preferred acid catalyst medium. Mixtures of the protonic and Lewis acid catalysts may be employed, for example $BF_3$ and $H_2SO_4$, but are not preferred.

Although the process of the present invention may be carried out in the absence of solvents, particularly, at the higher temperature of reaction, i.e., 100° C. and above, solvents or mixtures of solvents which are stable and chemically inert to the components of the reaction system may be and are generally employed due to the viscosity of the mixture of N-benzyl compounds in the form of dimers, trimers, tetramers, etc. Suitable solvents which are employed essentially in an anhydrous condition and generally in amounts of from 0 to 50 weight percent based on the reaction mixture include, for example, nitrated and halogenated aromatic hydrocarbons having up to 12 carbon atoms such as nitrobenzenes, nitrotoluenes, dichlorobenzene, dibromobenzene, alkanes and substituted alkanes, having up to 16 carbon atoms, such as n-pentanes, isopentane, n-hexane, 2-methylpentane, n-heptane, 3,4-dimethylhexane, 2-methylhexane, 3-ethylpentane, cyclopentane, cyclohexane, methylcyclohexane, ethylcyclopentane, cyclooctane, chloroform, carbon tetrachloride, dichloroethane, etc., lower aliphatic acids having up to 8 carbon atoms such as acetic, propionic, etc. and lower aliphatic alcohols having up to 8 carbon atoms such as methanol, ethanol, propanols, butanols, etc. Nitrobenzene, nitrotoluene and dichlorobenzene are the preferred solvents. Greater amounts of solvent, may be employed but generally are not necessary due to the added burden of recovery. While as indicated above, mixtures of solvents may be employed, it is preferable to use individual solvents in order to alleviate any recovery problem.

As indicated above, the reaction of the present invention can be suitably performed by charging the N-benzyl compounds contained in a condensate or otherwise, together with the protonic or Lewis acid catalyst and solvent into a suitable reactor while maintaining reaction conditions essentially anhydrous, and then heating the mixture to the desired temperature. The reaction will proceed at temperatures of from about 50° C. to 170° C. It is generally preferred to operate the process at temperatures of from 80° C. to 130° C. to obtain a convenient rate of reaction. Heating and/or cooling means may be employed interior and/or exterior of the reaction to maintain the temperature within the desired range.

The process of the present invention is generally carried out at atmospheric pressure although higher pressures may be used at the higher reaction temperatures. While they may be used there is no apparent value in employing subatmospheric pressures.

The reaction time is generally dependent upon the mixture of N-benzyl compounds being reacted, or condensate being processed, temperature and on the amount and type of acid catalyst being employed and will vary dependent on whether the process is continuous or batch but will generally range between about 2 minutes and several hours.

The following examples are provided to illustrate the invention in accordance with the principles of this invention but are not to be construed as limiting the invention in any way except as indicated by the appended claims.

Although the process of this invention will be directed primarily to the preparation of diphenylmethane dicarbamate, ethyl esters and the polymethylene polyphenyl carbamates, ethyl esters by the acid catalyzed conversion or rearrangement of (ethoxycarbonyl)-phenylaminomethylphenyl carbamic acid, ethyl ester, including the higher homolog trimers, tetramers, etc., which are produced for example as side products by the condensation of ethylphenylcarbamate and a carbonyl compound as hereinabove described, it is not intended that the process be limited to such (ethoxycarbonyl)-phenylaminomethylphenyl carbamic acid compounds and those skilled in the art will recognize that the present invention is broadly applicable to the treatment of other (alkoxycarbonyl)phenylaminomethylphenyl compounds such as the methyl and propyl esters and higher homologs.

In the Examples which follow, the reactions were run in 300 ml three neck glass reaction flasks fitted with a mechanical stirrer, reflux condenser, and thermometer. The reactants were charged to the flask and the flask immersed into a constant temperature oil bath. At the end of the reaction time, water was added to the flask to quench the reaction and extract the acid medium or the catalyst was removed and recovered by filtration. Conversion of the N-benzyl compounds charged and product yield and distribution was determined by high speed liquid chromatography.

EXAMPLE 1 (Comparative)

2-[(ethoxycarbonyl)phenylaminomethyl]phenylcarbamic acid, ethyl ester (N-benzyl compound) was prepared by reacting 10 g. of N-phenyl-2-aminobenzylamine (prepared by the method described in, Beilstein Organische Chemie, Volume XIII, System No. 1740–1871, page 166), with 1.2 g. of ethylchloroformate in the presence of 1 ml. pyridine and 50 ml. tetrahydrofuran as solvent for 1 hr. at 50° C. and then filtering to remove pyridine hydrochloride and evaporating the solvent.

0.3 g. of the N-benzyl compound prepared above along with 1.0 g. of 37 weight percent hydrochloric acid was heated at 100° C. for 60 minutes on a constant temperature bath. After completion of the reaction, 10 ml. water was added to quench the reaction and extract the hydrochloric acid medium. Analysis of the resulting reaction product by high speed liquid chromatography showed that 89 percent of unreacted N-benzyl compounds charged was recovered along with some ethylphenylcarbamate resulting from straight disassociation of the N-benzyl compound and other unidentified reaction by products. No rearrangement to diurethane products were detected.

EXAMPLE 2 (Comparative)

The procedure of Example 1 was repeated employing 0.3 g. of 2-[(ethoxycarbonyl)phenylaminomethyl]phenylcarbamic acid, ethyl ester, prepared as shown in Example 1, and 2.0 g. of 49 weight percent sulfuric acid. The mixture was charged to the reaction flask and heated to 100° C. for 60 minutes after which the reaction mixture was quenched with 10 ml water and the acid medium extracted. Chromatographic analysis showed that 99 percent of the 2-[(ethoxycarbonyl)phenylaminomethyl]phenylcarbamic acid, ethyl ester originally charged was recovered unchanged along with an undetermined amount of ethylphenylcarbamate and traces of the diethyl ester of 2,4'-methylenedicarbanilic acid.

EXAMPLE 3 (Comparative)

0.3 grams of a mixture of 2-[(ethoxycarbonyl)phenylaminomethyl]phenylcarbamic acid, ethyl ester and 4-[(ethoxycarbonyl)phenylaminomethyl]phenylcarbamic acid, ethyl ester (46 and 54 percent of the 2 and 4 isomer respectively) and prepared by reacting a mixture of N-phenyl-2- and 4-aminobenzylamine, made by the method described in British Pat. No. 1,177,557, with ethylchloroformate as described in Example 1 above, along with 1.0 g. of 60 weight percent sulfuric acid was charged to the reaction flask and heated at 110° C. for 60 minutes. Analysis showed that essentially all of the 4 isomer was converted to 4,4'-methylene(phenylcarbamic acid), diethyl ester but that 84 percent of the 2 isomer remained unchanged. The 2 isomer could not be separated from the reaction mixture to allow further processing of the desired diethyl ester urethane.

EXAMPLE 4

0.3 g. of an ethyl ester of 2-[(ethoxycarbonyl)-phenylaminomethyl]phenylcarbamic acid (N-benzyl compound), prepared as in Example 1, along with 1.0 g. of 96.4 weight percent concentrated sulfuric acid was charged to a 300 ml reaction flask. The mixture was heated to 100° C. on a constant temperature bath for 60 minutes. High speed liquid chromatographic analysis showed conversion of the ethyl ester of 2-[(ethoxycarbonyl)phenylaminomethyl]phenylcarbamic acid to the diethyl ester of 2,4'-methylenebis(phenylcarbamic) acid and higher homologs to be 99+ percent with minor amounts of ethylphenylcarbamate. After acid extraction with water, the resulting 2,4'-methylenebis(phenylcarbamic) acid, diethyl ester (diurethane) was subjected to thermal decomposition by the method described in U.S. Pat. No. 3,962,302 to produce the diphenylmethane-2,4'-diisocyanate in good yield.

EXAMPLE 5

Example 4 was repeated employing a mixture of 1.0 g. of the N-benzyl compound of Example 4 along with 3.7 g. of 96.4 weight percent concentrated sulfuric acid and 4.0 g. of absolute ethyl alcohol as solvent. The mixture was heated to a temperature of 90° C. for 70 minutes. Analysis showed that conversion of the N-benzyl compound to the diurethane was 95 percent with by-product ethylphenylcarbamate and other unidentified by products present.

EXAMPLE 6

A condensation product from the reaction of ethylphenylcarbamate with a 30 percent aqueous formaldehyde solution and 37 weight percent hydrochloric acid in water was prepared according to Example 2 of U.S. Pat. No. 2,946,768 and contained approximately 33 percent unreacted ethylphenylcarbamate, 38 percent diphenylmethane dicarbamates (2,4' - 4,4' -isomers), 4 percent triurethanes, 15 percent N-benzyl compound dimer (2 and 4-[(ethoxycarbonyl) phenylaminomethyl]-phenylcarbamic acid, ethyl ester), 8 percent N-benzyl compound trimers such as 4[(ethoxycarbonyl) phenylaminomethyl]-2,4' -methylenebis(phenylcarbamic acid) diethyl ester and a small amount of other unidentified by-products. 6.0 g. of the condensation reaction product along with 6.0 g. of nitrobenzene solvent and 2.0 g. of 96.4 weight percent sulfuric acid was charged to a reaction flask and heated at 80° C. for 30 minutes. After completion of the reaction and acid extraction, analysis of the product showed 100 percent conversion of the N-benzyl compound dimers and trimers to the desired methylene group bridged aromatic di- and triurethane compounds.

EXAMPLE 7 (Comparative)

Example 6 was repeated employing 6.0 g. of the same condensation reaction product along with 6.0 g. nitrobenzene solvent and 6.0 g. of 37 weight percent hydrochloric acid. The reaction was carried out at 120° C. for a period of 4 hours. Analysis of the product showed that only 2 percent of the contained N-benzyl compounds were arranged to di or triurethane products.

EXAMPLE 8 (Comparative)

Example 6 was repeated employing 6.0 g. of the same condensation reaction product along with 6.0 g. of nitrobenzene solvent and 6.0 g. of 47 weight percent sulfuric acid. The reaction was carried out at 90° C. for 2 hours. Analysis of the reaction product indicated that only 3 percent of the N-benzyl compounds were rearranged to di or triurethane products.

EXAMPLE 9

Example 6 was repeated employing 1.0 g. of the condensation reaction product from which essentially all of the unreacted ethylphenylcarbamate was removed by vacuum distillation, along with 4.0 g. of n-butanol and 3.7 g. of 96.4 weight percent sulfuric acid. The mixture was heated at 110° C. for 1 hour. Analysis of the rearrangement reaction product showed 100 percent conversion of the contained N-benzyl compound dimers and trimers to the desired urethanes.

EXAMPLE 10

A number of runs were carried out according to the procedures of Example 6 but employing 6 g. of a condensation reaction product of ethylphenylcarbamate with a 30 percent aqueous formaldehyde solution, 85 percent commercial grade phosphoric acid and water prepared by the process of U.S. Pat. No. 2,946,768. The condensation contained approximately 28.8 percent unreacted ethylphenylcarbamate, 42.4 percent diphenylmethane dicarbamates (2,4' and 4,4' isomers) 5 percent tri and higher polymeric urethanes, 16 percent N-benzyl compound dimers, 6 percent N-benzyl compound trimers and higher homologs. Various reaction conditions, solvents and acid catalyst were employed. The reaction product was analyzed by high speed liquid chromatography for the N-benzyl compound rearrangement. The results are set forth in the Table 1 below showing certain values in weight percent.

TABLE 1

| Run No. | Acid Catalyst (g.) | Solvent (g.) | Temp. ° C. | Time mins. | % N-benzyl Compound Conversion[1] |
|---|---|---|---|---|---|
| 1 | 96.4% $H_2SO_4$ (1.85 g.) | Absolute[2] Ethanol (6.0 g.) | 100 | 60 | 100 |
| 2 | 96.4% $H_2SO_4$ (2.00 g.) | n-butanol (6.0 g.) | 110 | 60 | 100 |
| 3[3] | 37% HCl (6.0 g.) | none | 100 | 240 | 11.5 |
| 4 | Anhyd. p-toluene Sulfonic Acid (3.60 g.) | Nitrobenzene (6.0 g.) | 120 | 30 | 100 |
| 5 | Anhyd. p-toluene Sulfonic Acid (6.0 g.) | Dichlorobenzene (6.0 g.) | 100 | 60 | 97 |
| 6 | "Amberlyst-15"[4] 4.9 meq $H^+$/g. (2.00 g.) | Nitrotoluene (6.0 g.) | 120 | 30 | 87 |
| 7 | $HSO_3F$ (2.00 g.) | Nitrobenzene (6.0 g.) | 100 | 60 | 99 |
| 8 | 96.4% $H_2SO_4$ (3.00 g.) | Nitrobenzene (6.0 g.) | 90 | 30 | 100 |
| 9 | 96.4% $H_2SO_4$ (1.85 g.) | Nitrobenzene (6.0 g.) | 100 | 30 | 100 |
| 10 | 96.4% $H_2SO_4$ (0.65 g.) | Nitrobenzene (6.0 g.) | 100 | 60 | 76.8 |
| 11 | 96.4% $H_2SO_4$ (1.85 g.) | n-hexane[2] (6.0 g.) | 110 | 60 | 96.5 |
| 12 | 75% $H_2SO_4$ (12.0 g.) | Nitrobenzene (6.0 g.) | 80 | 30 | 98 |

[1]Total per cent conversion of dimers, trimers, tetramers, etc. contained in condensate.
[2]Reacted under 50 psig pressure.
[3]Comparative run.
[4]"Amberlyst-15" (a Trademark of Rohm and Haas) - A strongly acidic sulfonated polyaromatic ion exchange resin described hereinabove.

EXAMPLE 11

A run was carried out using 6 g. of a condensation reaction product of ethylphenylcarbamate with trioxane (98 percent) and 60 percent aqueous sulfuric acid. The condensate contained approximately 20 percent unreacted ethylphenylcarbamate, 44 percent diphenylmethane dicarbamates (2,4' and 4,4' isomers), 10 percent tri- and higher polymeric urethanes, 12 percent N-benzyl compound dimers and 13 percent N-benzyl trimers and higher homologs and a small amount of unidentified by-products. The condensation product was dissolved in 6.0 g. of nitrobenzene and contacted with 0.70 g. of anhydrous iron (III) chloride for 30 minutes at 100° C. The reaction was quenched with water and the iron catalyst was extracted from the organic product by water washing. Rearrangement of N-benzyl compounds was 100 percent as determined by high speed liquid chromatography of the product.

EXAMPLE 12

A number of runs were made according to the procedure of Example 11 using 6.0 g. nitrobenzene solvent in each run. Various reaction conditions and Lewis acid catalysts were employed. The catalyst was recovered from the product mixture by filtration or extracted by water washing and the reaction product analyzed by high speed liquid chromatography for N-benzyl compound rearrangement. The results are set forth in Table 2.

TABLE 2

| Run No. | Acid Catalyst (g.) | Temp. ° C. | Time Min. | % N-Benzyl[4] Conversion |
|---|---|---|---|---|
| 1 | Iron(III)chloride[1] (0.67 g.) | 80 | 30 | 60 |
| 2 | Iron(III)chloride[3] (0.09 g.) | 150 | 15 | 50 |
| 3 | Aluminum chloride[1] (1.20 g.) | 120 | 60 | 59 |
| 4 | Antimony pentafluoride[2] (27% antimony) supported on graphite (0.7 g.) | 120 | 60 | 100 |
| 5 | Antimony pentafluoride[2] (27% antimony) supported on graphite (0.11 g.) | 120 | 30 | 85 |
| 6 | Boron-trifluoride[3] etherate (48% boron trifluoride) (2.3 g.) | 120 | 60 | 94 |
| 7 | Aluminum chloride[2] (7% aluminum) supported on graphite (0.8 g.) | 120 | 60 | 57 |

[1]Lewis acid filtered and water washed.
[2]Lewis acid filtered to recover.
[3]Water washed to extract
[4]Total per cent conversion of dimers, trimers, tetramers, etc.

We claim:
1. A process for the preparation of a diphenylmethane mono and dicarbamate and polymethylene polyphenyl carbamate homologs and derivatives which comprises reacting under substantially anhydrous conditions, an (alkoxycarbonyl) phenylaminomethylphenyl compound having the formula

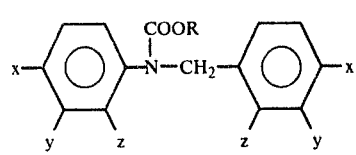

and the higher homologs of said compounds, wherein x, y and z, which are different on the ring are an alkyl group of from 1 to 3 carbon atoms, an —NHCOOR, —CH$_2$ArNHCOOR or —N(COOR)CH$_2$Ar group, R is a 1 to 3 carbon alkyl group and Ar is phenyl which may be substituted with an alkyl group of from 1 to 3 carbon atoms; x, y and z may also be at least one hydrogen, at a temperature in the range of from about 50° C. to 170° C. in the presence of an effective amount of a protonic acid catalyst having a strength of at least the magnitude of a 75 percent sulfuric acid, or a Lewis acid having a concentration of at least 0.5 weight percent based on the total reaction mixture, to rearrange the (alkoxycarbonyl) phenylaminomethylphenyl compounds to the mono and dicarbamates and polymethylene polyphenylcarbamates and derivatives and recovering the desired carbamates.

2. A process according to claim 1 wherein the (alkoxycarbonyl)phenylaminomethylphenyl compound is derived from the condensation reaction of an N-arylcarbamic acid ester with a carbonyl compound in the presence of a dilute aqueous acid solution.

3. A process according to claim 2 wherein the N-arylcarbamic acid ester is ethylphenylcarbamate.

4. A process according to claim 2 wherein the carbonyl compound is formaldehyde.

5. A process according to claim 1 wherein the (alkoxycarbonyl)phenylaminomethylphenyl compound is the ethyl ester of 2-[(ethoxycarbonyl) phenylaminomethyl]-phenylcarbamic acid or 4-[(ethoxycarbonyl)-phenylaminomethyl]phenylcarbamic acid.

6. A process according to claim 1 wherein the protonic acid catalyst is an inorganic or organic acid and is employed in concentrations of from 0.1 to 25 weight percent based on the reaction mixture.

7. A process according to claim 6 wherein the concentration is from 1 to 10 weight percent.

8. A process according to claim 6 wherein the protonic acid catalyst is selected from the group consisting of sulfuric acid, p-toluenesulfonic acid, trifluoromethane sulfonic acid, anhydrous hydrofluoric acid, fluorosulfonic acid and strongly acidic sulfonated polyaromatic ion exchange resins.

9. A process according to claim 8 wherein the acid catalyst is sulfuric acid.

10. A process according to claim 1 wherein the reaction is carried out in the presence of a solvent selected from the group consisting of nitrated and halogenated hydrocarbons having up to 12 carbon atoms, alkanes and substituted alkanes having up to 16 carbon atoms, lower aliphatic acids and lower aliphatic alcohols having up to 8 carbon atoms.

11. A process according to claim 10 wherein the solvent is nitrobenzene, nitrotoluene or dichlorobenzene.

12. A process according to claim 11 wherein the solvent is nitrobenzene.

13. A process according to claim 1 wherein the reaction is carried out at a temperature in the range of from about 80° C. to 130° C.

14. A process for the preparation of a diphenylmethane dicarbamate, diethyl ester, which comprises reacting the ethyl ester of 2-[(ethoxycarbonyl) phenylaminomethyl]-phenylcarbamic acid or 4-[(ethoxycarbonyl)phenylaminomethyl]-phenylcarbamic acid derived from the condensation reaction of ethylphenylcarbamate with a carbonyl compound in the presence of a dilute aqueous acid solution, at atmospheric pressure and at a temperature in the range of from about 80° C. to 130° C. in the presence of sulfuric acid having a strength of between 75 and 100 percent and recovering the desired diphenylmethane dicarbamates.

15. A process according to claim 1 wherein the Lewis acid catalyst is selected from the group consisting of tin(IV) chloride, iron (III)chloride, aluminum chloride, antimony pentafluoride and boron trifluoride.

16. A process according to claim 1 wherein the Lewis acid is employed in concentrations of from 0.5 to 20 weight percent based on the total reaction mixture.

17. A process according to claim 1 wherein the Lewis acid catalyst is supported.

18. A process according to claim 17 wherein the support is graphite.

19. A process for the preparation of a diphenylmethane dicarbamate, diethyl ester, which comprises reacting the ethyl ester of 2-[(ethoxycarbonyl) phenylaminomethyl]-phenylcarbamic acid or 4-[(ethoxycarbonyl) phenylaminomethyl]-phenylcarbamic acid derived from the condensation reaction of ethylphenylcarbamate with a carbonyl compound in the presence of a dilute aqueous acid solution, at atmospheric pressure and at a temperature in the range of from about 80° C. in the presence of antimony pentafluoride having a concentration of from 0.5 to 20 weight percent based on the total reaction mixture, and recovering the desired diphenylmethane dicarbamates.

* * * * *

UNITED STATES PATENT OFFICE
CERTIFICATE OF CORRECTION

PATENT NO. : 4,146,727
DATED : March 27, 1979
INVENTOR(S) : E. T. Shawl and J. G. Zajacek It is certified that error appears in the above—identified patent and that said Letters Patent are hereby corrected as shown below:

Column 1, line 12, should read:

"tion Ser. No. 838,691, filed Oct. 3, 1977, now abandoned."

Column 12, Claim 19, line 42, should read:

" and at a temperature in the range of from about 80°C. to 130°C."

Signed and Sealed this

Thirtieth Day of October 1979

[SEAL]

Attest:

RUTH C. MASON
Attesting Officer

LUTRELLE F. PARKER
Acting Commissioner of Patents and Trademarks